(12) United States Patent
Ishiguro et al.

(10) Patent No.: US 10,293,183 B2
(45) Date of Patent: May 21, 2019

(54) PARTICLE BEAM TREATMENT SYSTEM (71) Applicant: Hitachi, Ltd., Tokyo (JP)

(72) Inventors: Naofumi Ishiguro, Tokyo (JP); Isao Furuse, Tokyo (JP); Tomoaki Hirane, Tokyo (JP); Haruki Arita, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/157,469

(22) Filed: May 18, 2016

(65) Prior Publication Data

US 2016/0346567 A1 Dec. 1, 2016

(30) Foreign Application Priority Data

May 27, 2015 (JP) .................................. 2015-107826

(51) Int. Cl.
*A61N 5/10* (2006.01)

(52) U.S. Cl.
CPC ......... *A61N 5/1048* (2013.01); *A61N 5/1079* (2013.01); *A61N 2005/1087* (2013.01)

(58) Field of Classification Search
CPC ...................... A61N 5/1048; A61N 2005/1087
USPC ................................ 250/492.1, 492.2, 492.3
See application file for complete search history.

(56) References Cited

U.S. PATENT DOCUMENTS

| 2006/0113487 A1 | 6/2006 | Naumann et al. |
| 2006/0219948 A1 | 10/2006 | Ueno et al. |
| 2007/0018121 A1 | 1/2007 | Leyman et al. |
| 2007/0114471 A1 | 5/2007 | Birgy et al. |

FOREIGN PATENT DOCUMENTS

| EP | 1 454 657 A2 | 9/2004 |
| EP | 2 505 231 A1 | 10/2012 |
| JP | 2007-501084 A | 1/2007 |
| JP | 2011-182866 A | 9/2011 |
| WO | 2004101070 A1 | 11/2004 |

OTHER PUBLICATIONS

Extended European Search Report received in corresponding European Application No. 16169995.4 dated Oct. 5, 2016.

*Primary Examiner* — Nicole M Ippolito
*Assistant Examiner* — Hanway Chang
(74) *Attorney, Agent, or Firm* — Mattingly & Malur, PC (57) ABSTRACT

An object of the present invention is to provide a particle beam treatment system that can realize the reduction of treatment time for a specific patient, compared with treatment time in a conventional type. A control unit of a control system controls a beam routing system and irradiation devices so as to maintain the occupation of an accelerator when a certain treatment room of plural treatment rooms once occupies the accelerator except intentional operation to release the occupation of the accelerator or the occurrence of system failure.

19 Claims, 6 Drawing Sheets

PARTICLE BEAM TREATMENT SYSTEM

BACKGROUND

The present invention relates to a particle beam treatment system suitable for particle beam treatment that utilizes a charged particle beam (an ion beam) such as a proton and a heavy ion, especially relates to technique related to a particle beam treatment system that can realize therapeutic irradiation on a certain specific patient in short time.

For one example of a method and a system for automatically assigning a particle beam to one of plural irradiation chambers, Japanese Unexamined Patent Application Publication (Translation of PCT Application) No. 2007-501084 discloses technique that the system checks whether the corresponding beam is available or not when a request from one of beam users is received and automatically assigns the beam to the requested irradiation chamber. If not available, the request is located in a certain position in a waiting list of pending requests and the position varies depending upon a priority level (and arrival time) linked with requests.

SUMMARY

For radiotherapy for cancer, particle beam treatment for remedying by irradiating an affected part by cancer of a patient with an ion beam such as a proton and a heavy ion is known. For an ion beam irradiation method, a scanning irradiation method can be given. There is an operating method of realizing a request for assigning anion beam to plural irradiation chambers in such a particle beam treatment system.

When particle beam treatment is applied to a certain patient, a prescription for treatment proper to the patient exists. The prescription for treatment includes one or plural patient positioning fields, one or plural imaging fields and one or plural remedial irradiation fields.

The patient positioning field provides the movement of the patient to a prescribed remedial position. Further, the imaging field is provided to image an affected part to be a target of treatment by X-rays, CT, and the like and to verify that the patient is located in the remedial position prescribed in the prescription for treatment. Moreover, the remedial irradiation field is provided to irradiate the affected part to be the target of the treatment of the patient with an ion beam prescribed in the prescription for treatment. In addition, the patient positioning field and the imaging field can be included in the remedial irradiation field by managing the movement and the imaging of the patient in the remedial irradiation field.

The corresponding treatment room is required to occupy an accelerator that accelerates an ion beam in exceeding such the remedial irradiation field. When a certain patient terminates a remedial irradiation field in a certain treatment room, occupation of the occupied accelerator is released independent of whether an unexecuted remedial irradiation field exists in a prescription for the patient or not. The accelerator the occupation of which is released is occupied by another treatment room in an occupation waiting state or becomes available until a request for newly occupying a treatment room is made when there is no treatment room in occupation waiting state.

When a prescription for a certain patient includes plural remedial irradiation fields, the occupation of an accelerator once occupied in the remedial irradiation field is required to be necessarily released when the remedial irradiation field is terminated in executing the prescription for the patient, and it is conceivable that the accelerator is occupied by another treatment room until the next unexecuted remedial irradiation field is executed since a certain remedial irradiation field is terminated. At that time, it is required to wait for the release of the occupation by another treatment room of the accelerator in order to execute the unexecuted remedial irradiation field with the prescription for the patient.

In this case, there are various patients who desire particle beam treatment and various special circumstances including a case where for example, an infant patient and a patient to whom narcotics are applied before treatment cannot endure long-time treatment are conceivable. As described above, it is a subject to reduce the treatment time (the constraint time for taking particle beam treatment) of the patient who is difficult to endure long-time treatment.

In such a case, such a method of prioritizing treatment and assigning the occupation of the accelerator on the basis of the priority as disclosed in the Japanese Unexamined Patent Application Publication (Translation of PCT Application) No. 2007-501084 can be applied. However, in a case where priority of all remedies is the upmost in a system and in a case where the occupation of the accelerator is once released between treatments and the accelerator is used for the treatment of another treatment room even if higher precedence than another treatment room is given, there is a problem that the release of the occupation by another treatment of the accelerator is required to be awaited and the reduction of treatment time of a specific patient has a limit.

An object of the present invention is to provide a particle beam treatment system that can realize the reduction of treatment time of a specific patient, compared with a conventional type.

To settle the abovementioned problem, configuration disclosed in a scope of claims for example will be adopted.

The present invention includes plural device, equipment, and systems for settling the problem. For example, the present invention is provided with an accelerator that radiates a charged particle beam, plural treatment rooms in each of which an irradiation device that radiates the charged particle beam is arranged, a beam routing system which is connected to the accelerator and which separately routes the charged particle beam radiated from the accelerator to each irradiation device in the plural treatment rooms, and a control system that controls the accelerator, the beam routing system, and the irradiation device. The control system controls the beam routing system and the irradiation device so as to maintain the occupation of the accelerator except intentional operation for releasing the occupation of the accelerator or the occurrence of system failure when a certain treatment room of the plural treatment rooms once occupies the accelerator except intentional operation to release the occupation of the accelerator or the occurrence of system failure.

According to the present invention, the more reduction of treatment time of a specific patient can be realized.

DETAILED DESCRIPTION

Figure 1:
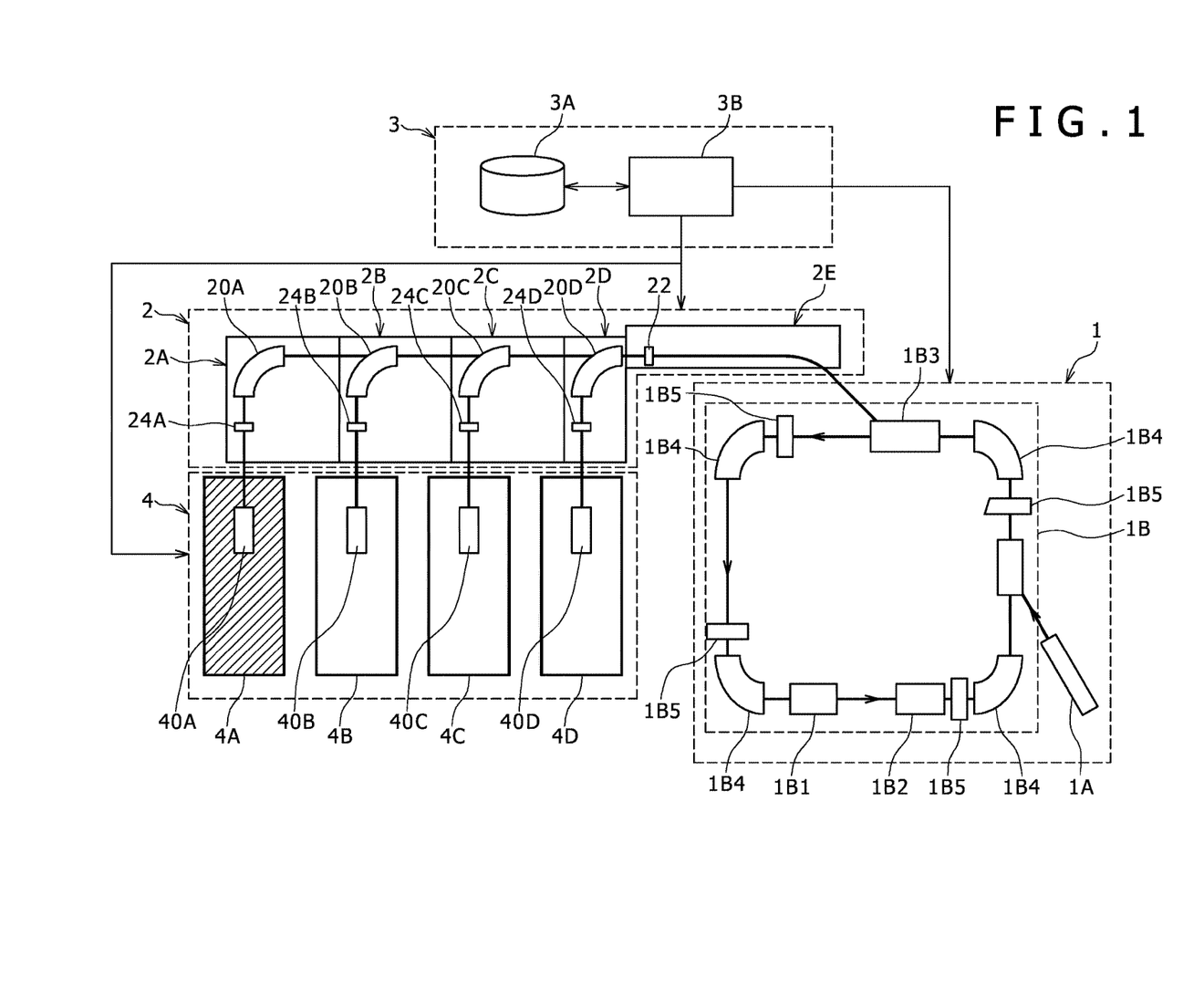
FIG. 1 shows one example of the configuration of a particle beam treatment system equivalent to an embodiment of the present invention.
Figure 2A:
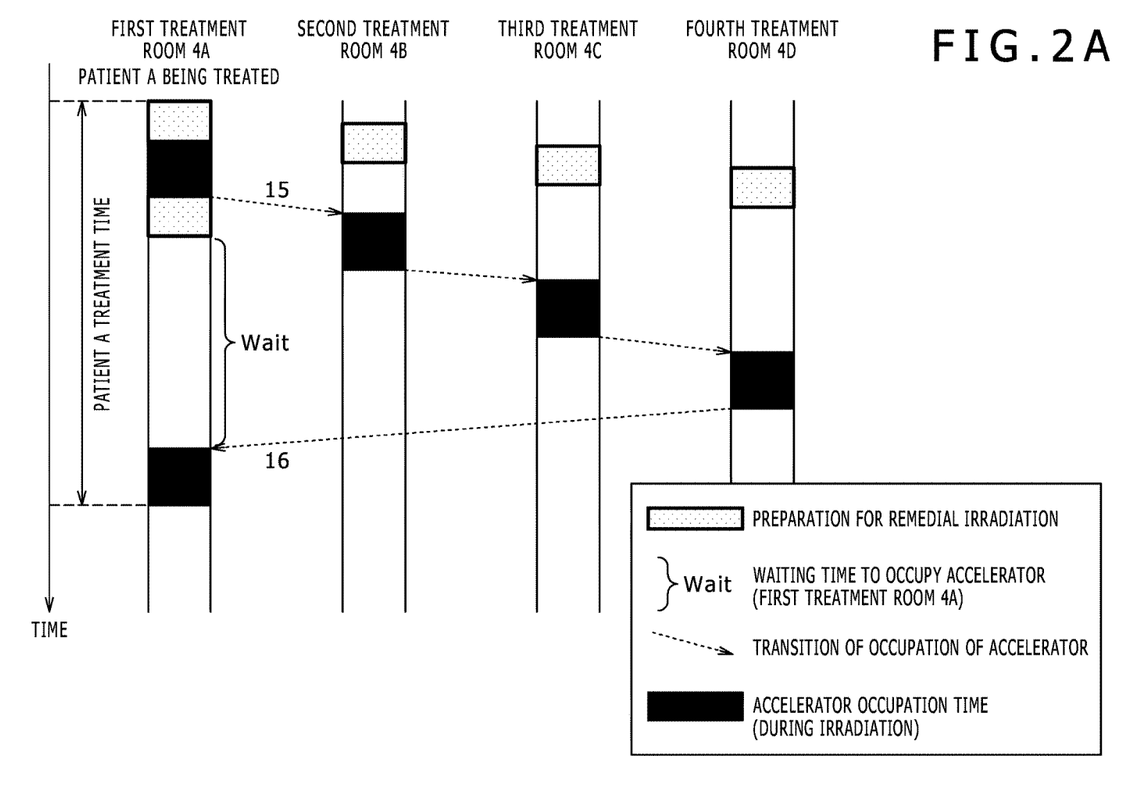
FIG. 2A shows one example (a case where the precedence in occupation of an accelerator of all treatment rooms is the same) of waiting time in a first treatment room under general discontinuous multiportal irradiation control.
Figure 2B:
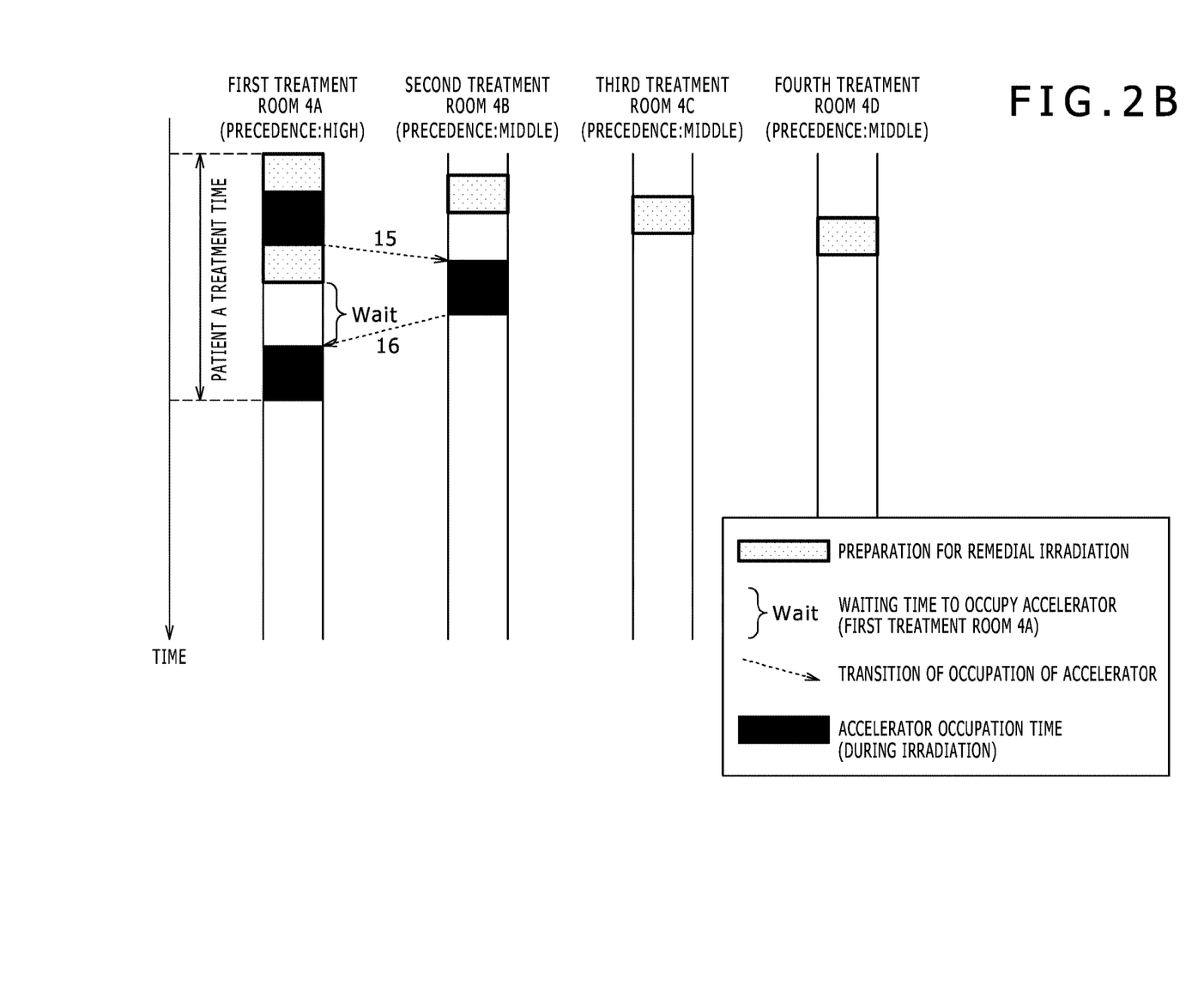
FIG. 2B shows one example (a case where the first treatment room has higher precedence of the occupation of the accelerator than the precedence of the other treatment rooms) of waiting time in the first treatment room under the general discontinuous multiportal irradiation control.
Figure 3:
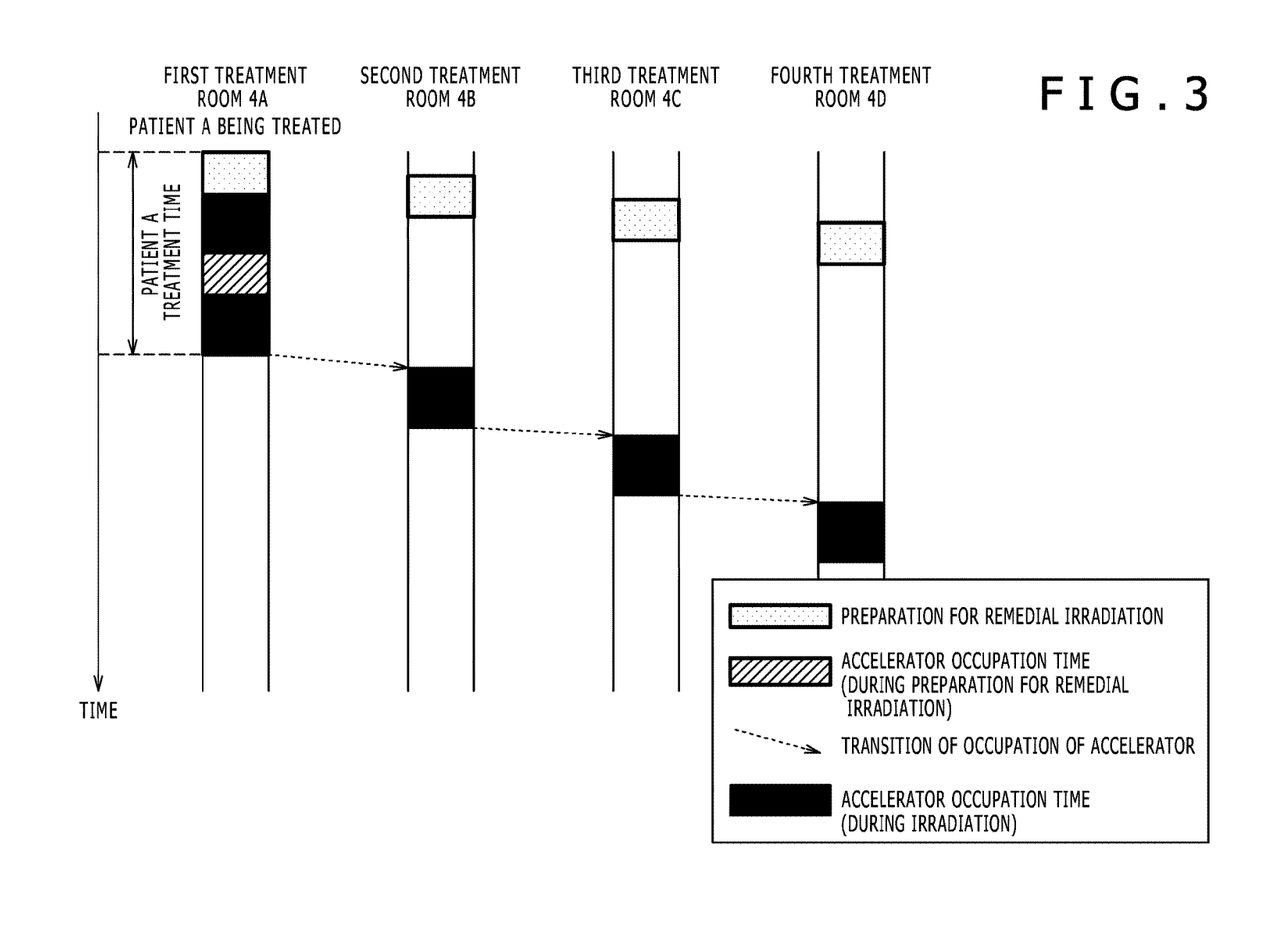
FIG. 3 shows one example of waiting time in a first treatment room under continuous multiportal irradiation control in the embodiment of the present invention.
Figure 4:
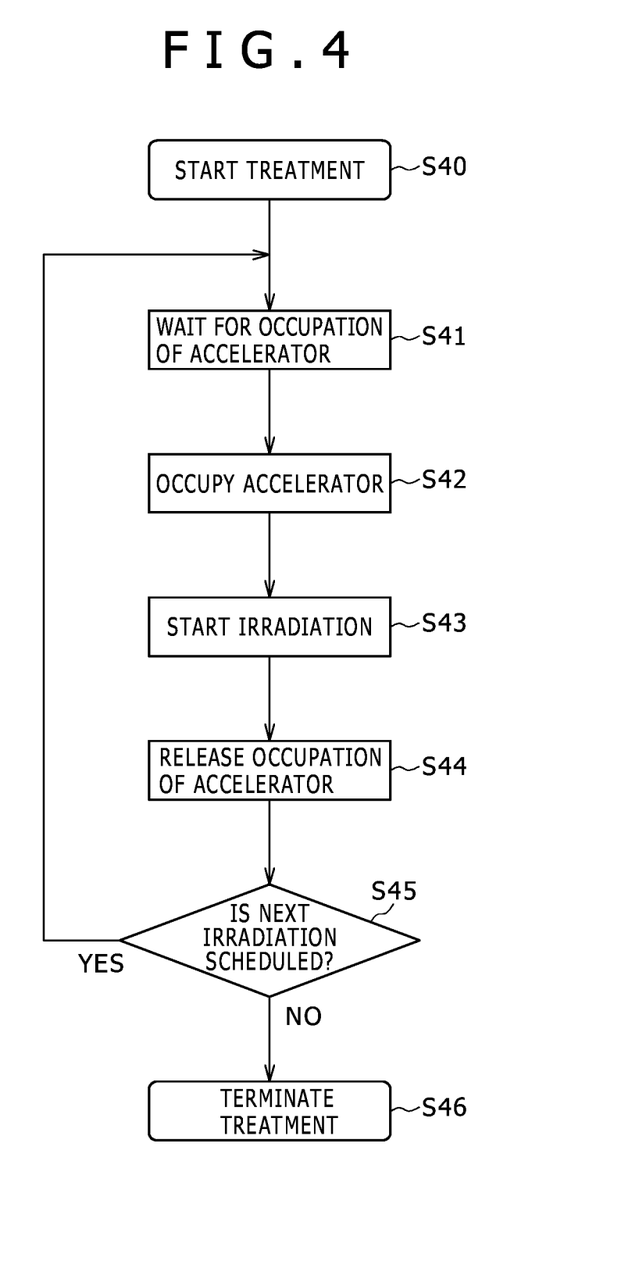
FIG. 4 is a flowchart in remedial irradiation under the general discontinuous multiportal irradiation control.
Figure 5:
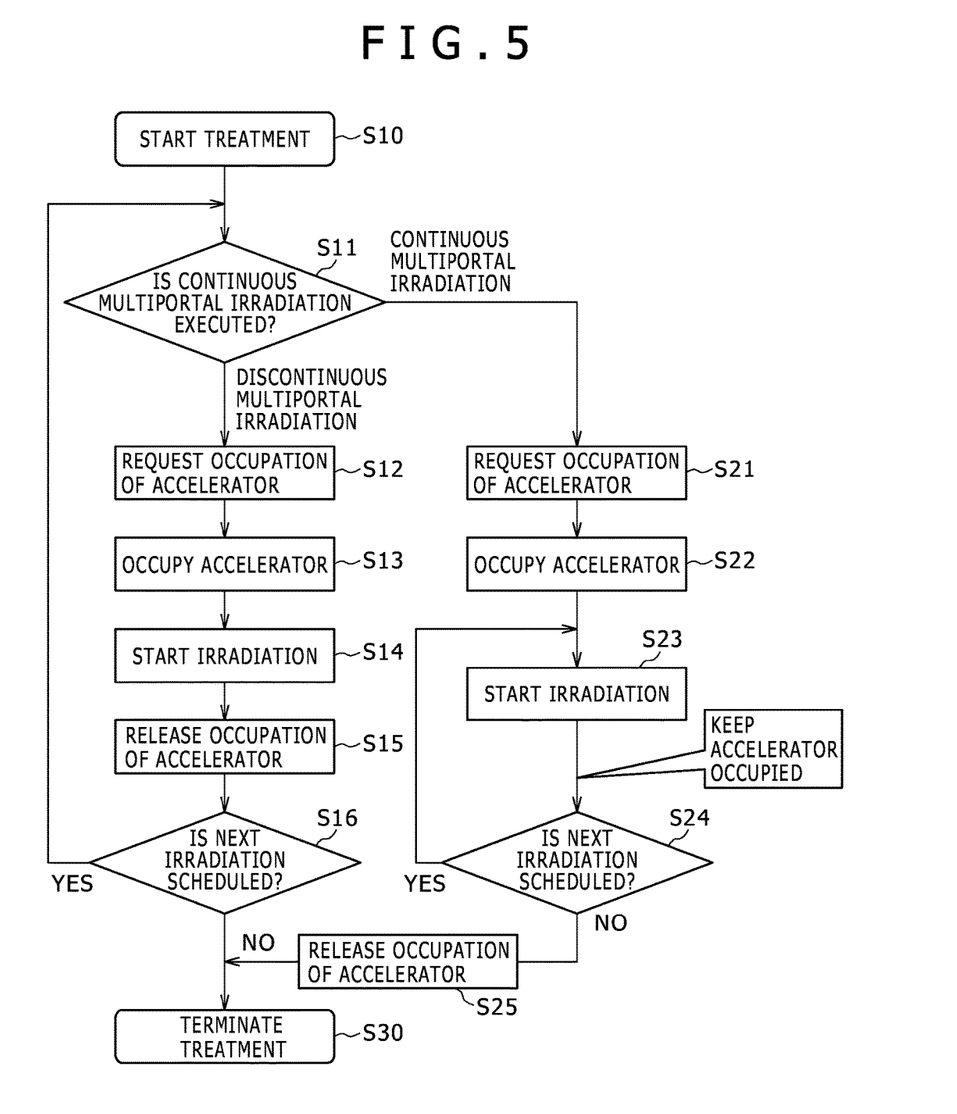
FIG. 5 is a flowchart in remedial irradiation under the continuous multiportal irradiation control in the embodiment of the present invention.

Referring to FIGS. 1 to 5, an embodiment of a particle beam treatment system according to the present invention will be described below. FIG. 1 shows one example of the configuration of the particle beam treatment system equivalent to the embodiment of the present invention, FIG. 2A shows one example (a case where the precedence in occupation of an accelerator of all treatment rooms is the same) of waiting time in a first treatment room under the general discontinuous multiportal irradiation control, FIG. 2B shows one example (a case where the first treatment room has higher precedence of the occupation of the accelerator than the precedence of the other treatment rooms) of waiting time in the first treatment room under the general discontinuous multiportal irradiation control, FIG. 3 shows one example of waiting time in a first treatment room under the continuous multiportal irradiation control in the embodiment of the present invention, FIG. 4 is a flowchart in remedial irradiation under the general discontinuous multiportal irradiation control, and FIG. 5 is a flowchart in remedial irradiation under the continuous multiportal irradiation control in the embodiment of the present invention.

First, each term in this embodiment will be described.

In the present invention, the occupation of the accelerator means a state in which the accelerator can be exclusively used to accelerate a desired beam when an ion beam irradiates a remedial field (described later) in a certain treatment room of plural treatment rooms. When the certain treatment room occupies the accelerator, another treatment room cannot occupy the accelerator.

Further, a request for occupying the accelerator means a state in which a request that the certain treatment room should occupy the accelerator is made to a control system so as to occupy the accelerator. The control system that receives the request for occupying the accelerator turns the treatment room a state in which the treatment room occupies the accelerator or awaiting state for the occupation of the accelerator according to its own method and a situation at that time.

Moreover, waiting for the occupation of the accelerator means a state in which a request for occupying the accelerator in the certain treatment room is made to the control system and the treatment room waits for the occupation of the accelerator. There may be plural treatment rooms waiting for the occupation of the accelerator simultaneously.

In addition, the release of the occupation of the accelerator means a state in which the certain treatment room goes out of the occupation of the accelerator. It is when operation in a remedial irradiation field is finished in the treatment room in a state in which the accelerator is occupied, when failure is detected and irradiation is forcedly terminated by an interlocking system and when an authorized operator performs intentional operation to release the occupation of the accelerator that the occupation of the accelerator is released.

Further, the remedial field means a field for remedial irradiation. In the field, the accelerator is occupied, an ion beam is radiated, and treatment in the field is completed by the completion of irradiation, abnormal termination or intentional termination by an authorized operator.

Furthermore, a positioning field means a field for positioning a patient. This positioning field does not require the occupation of the accelerator and irradiation with an ion beam.

Furthermore, an imaging field means a field for acquiring image data. This imaging field does not require the occupation of the accelerator and irradiation with an ion beam.

Furthermore, preparation for remedial irradiation means work required for irradiation and executable without the occupation of the accelerator in the positioning field, the imaging field, and the like.

Furthermore, the precedence of occupying the accelerator means an index used for the control system to determine a treatment room that next occupies the accelerator when plural treatment rooms waiting for the occupation of the accelerator exist. The precedence of occupying the accelerator can also be assigned every treatment room beforehand and the precedence of occupying the accelerator can also be precedently assigned to a treatment room waiting for the occupation of the accelerator in advance.

Next, the particle beam treatment system equivalent to this embodiment will be described, referring to FIG. 1.

The particle beam treatment system in this embodiment is provided with an accelerator 1, four treatment rooms 4A, 4B, 4C, 4D (hereinafter also called the treatment room 4), a beam routing system 2 connected on the downstream side of the accelerator 1 and a control system 3 as shown in FIG. 1.

The accelerator 1 is equipment for accelerating and radiating an ion beam and is provided with an ion source (not shown), a preceding-stage accelerator (for example, a linear accelerator) 1A and a synchrotron 1B as a circular accelerator. In place of the synchrotron 1B, an accelerator without a preceding-stage accelerator such as a cyclotron and a linear accelerator may also be used.

The beam routing system 2 is provided with a first beam routing subsystem 2E, second beam routing subsystems 2A, 2B, 2C, 2D, switching electromagnets (route switching elements) 20A, 20B, 20C, 20D, shutters every treatment room 24A, 24B, 24C, 24D, and a shutter 22 common to all the treatment rooms.

The first beam routing subsystem 2E is a common beam routing subsystem connected to the accelerator 1 for respectively conducting an ion beam radiated from the accelerator 1 to the second beam routing subsystems 2A, 2B, 2C, 2D.

The second beam routing subsystems 2A, 2B, 2C, 2D are connected to the first beam routing subsystem 2E and are branched from the first beam routing subsystem 2E to separately route the ion beam routed by the first beam routing subsystem 2E to each irradiation device 40A, 40B, 40C, 40D in plural treatment rooms 4A, 4B, 4C, 4D.

The switching electromagnets 20A, 20B, 20C, 20D are arranged in each joint of a beam path of the first beam routing subsystem 2E and a beam path in the plural second beam routing subsystems 2A, 2B, 2C, 2D, are an electromagnet for switching the beam path for conducting the ion beam, and are one type of a deflecting electromagnet.

The shutters 24A, 24B, 24C, 24D are respectively provided to the plural second beam routing subsystems 2A, 2B, 2C, 2D and interrupt the beam path in the corresponding second beam routing subsystems 2A, 2B, 2C, 2D. The shutter 22 is provided to the first beam routing subsystem 2E and interrupts the beam path in the first beam routing subsystem 2E.

The treatment rooms 4A to 4D are respectively provided with the irradiation devices 40A to 40D respectively attached to a rotary gantry (not shown) installed inside. The treatment rooms 4A to 4D are first to fourth treatment rooms for a cancer patient, for example.

The irradiation devices 40A to 40D are equipment for irradiating with an ion beam and are provided with two scanning electromagnets that independently scan the beam in two orthogonal directions (hereinafter defined as lateral directions together) in a plane perpendicular to an orbit of the beam, a beam monitor, and the like.

The case where all the four treatment rooms have the same configuration has been described. However, all the four treatment rooms are not necessarily required to have the same configuration, and plural treatment rooms having separate configuration suitable for each treatment may also be provided. For example, the irradiation device may also be provided with a deflecting electromagnet, a scatterer, a ring collimator, a patient-side collimator, a bolus, and the like and may also be provided with another configuration. Further, the case where the irradiation devices 40A to 40D are attached to a rotary gantry so as to enable irradiating an affected part with a beam from an arbitrary direction has been described. However, the irradiation devices may also be fixed. When a treatment room suitable for continuous multiportal irradiation control described later and a treatment room not necessarily suitable are arranged, the preset invention can be applied to the treatment room suitable for the continuous multiportal irradiation control and general discontinuous multiportal irradiation control can be applied to the other treatment room.

The control system 3 is provided for controlling the accelerator 1, the beam routing system 2, and the irradiation devices 40A, 40B, 40C, 40D and is provided with a storage 3A and a control unit 3B. The control system 3 is connected to the beam routing system 2, the accelerator 1 and the treatment rooms 4, and the control unit 3B controls each equipment configuring the beam routing system 2, the accelerator 1 and the treatment rooms 4 (the irradiation devices 40A to 40D, each equipment in the beam routing system 2 including the switching electromagnets 20A to 20D, the shutters 24A to 24D and the shutter 22, and each equipment including the preceding-stage accelerator 1A and the synchrotron 1B) using various control parameters stored in the storage 3A.

Further, in this embodiment, the control unit 3B of the control system 3 controls the beam routing system 2 and the irradiation devices 40A, 40B, 40C, 40D so that the occupation of the accelerator 1 is maintained except intentional operation to release the occupation of the accelerator and the occurrence of system failure when the certain treatment room 4A, 4B, 4C, 4D of the plural treatment rooms 4A, 4B, 4C, 4D once occupies the accelerator 1 (hereinafter, control for maintaining the occupation of the accelerator 1 will also be called continuous multiportal irradiation control).

For example, the control unit 3B of the control system 3 executes continuous multiportal irradiation control until treatment prescribed a specific patient is completed when the specific patient is remedied in the certain treatment room 4A, 4B, 4C, 4D.

Or, the control unit 3B of the control system 3 executes continuous multiportal irradiation control until predetermined irradiation is completed when the specific treatment room 4A, 4B, 4C, 4D once occupies the accelerator 1 for remedial irradiation on the basis of the selection of a therapist who applies particle beam treatment to a patient.

Or, the control unit 3B of the control system 3 executes continuous multiportal irradiation control so that the occupation of the accelerator in the specific treatment room 4A, 4B, 4C, 4D is maintained when the specific treatment room 4A, 4B, 4C, 4D of the plural treatment rooms 4A, 4B, 4C, 4D occupies the accelerator 1.

Or, the control unit 3B of the control system 3 executes continuous multiportal irradiation control until the treatment of a specific prescription is completed when the specific prescription is applied to a patient in the unspecified treatment room 4A, 4B, 4C, 4D.

Further, the control unit 3B of the control system 3 controls so that a state maintaining the same operation is kept without changing control parameters of the switching electromagnets 20A, 20B, 20C, 20D and the shutters 24A, 24B, 24C, 24D while the occupation of the accelerator 1 is maintained.

When control which is not continuous multiportal irradiation control is selected, the control unit 3B of the control system 3 executes discontinuous multiportal irradiation control. In the discontinuous multiportal irradiation control at that time, well-known control such as the occupation of the accelerator in the order of arrival and the occupation of the accelerator on the basis of precedence can be executed.

Next, intentional operation to release the occupation of the accelerator or the occurrence of system failure will be described. The intentional operation to release the occupation of the accelerator means operation for activating an emergency stop button (an interlock) provided to the control system 3 when a therapist who applies particle beam treatment to a patient judges that the therapist had better stop the irradiation of an ion beam, for example, in emergency in which a condition of the patient rapidly changes. Further, time at which the system fails means time at which an interlocking system (not shown) independent of the control system 3 so as to secure the safety of a patient receives a signal showing that a state of each equipment in the beam routing system 2, the accelerator 1 and the treatment room 4 is abnormal and time at which the abnormality of a beam on the beam monitor in the treatment room 40A, 40B, 40C, 40D is detected. In these cases, the control unit 3B of the control system 3 receives an abnormality signal from the interlocking system as a beam radiation stop instruction and stops the application of a high frequency signal for radiation to a high frequency applying device for radiation 1B2 provided to the synchrotron 1B. Hereby, the synchrotron 1B stops the radiation of an ion beam. The stop of an ion beam may also be made by operating the shutter 24A, 24B, 24C, 24D and the shutter 22.

Next, the details of the abovementioned continuous multiportal irradiation control will be described, comparing with discontinuous multiportal irradiation control generally executed at the current time. In this case, waiting time in the first treatment room 4A will be described for an example.

While irradiation with an ion beam is made in a remedial irradiation field in the first treatment room 4A, the accelerator 1 supplies no ion beam to the treatment rooms (the second treatment room 4B, the third treatment room 4C, the fourth treatment room 4D) except the first treatment room 4A. Therefore, even if a request for occupying the accelerator in the treatment room except the corresponding first treatment room 4A is output to the control system 3, the release of the occupation of the accelerator by the first treatment room 4A that occupies the accelerator is required to be awaited so as to occupy the accelerator for irradiation. To release the occupation of the accelerator by the first treatment room 4A, it is required to finish the current remedial irradiation field in the first treatment room 4A. The remedial irradiation field is finished by finishing remedial irradiation scheduled in the remedial irradiation field or by intentionally stopping the field or by forced termination due to occurrence of failure.

In the case of general discontinuous multiportal irradiation control, when a remedial field is finished in the first treatment room 4A, the occupation of the accelerator in the first treatment room 4A is released. At this time, the accelerator 1 is occupied by the treatment room that requests the occupation (15 shown in FIGS. 2A, 2B) by a request for occupying the accelerator by another treatment room in a state in which the occupation of the accelerator is released. Then, to irradiate for remedy in the first treatment room 4A again, that is, to occupy the accelerator (16 shown in FIGS. 2A, 2B), the occupation of the accelerator is required to be awaited according to an accelerator occupation flow of the control system 3 of the particle beam treatment system.

The accelerator occupation flows of the control system 3 are diverse, and a method on the basis of "precedence of first arrival" shown in FIG. 2A and a method on the basis of "a prior level" shown in FIG. 2B can be given. The control system 3 determines the order of plural requests for occupying the accelerator by a predetermined method and outputs an instruction to occupy the accelerator to the switching electromagnet 20A, 20B, 20C, 20D so that an ion beam is incident on the corresponding course.

While another treatment room occupies the accelerator at the time at which preparation for next irradiation in the first treatment room 4A is completed even if the first treatment room 4A is at the upmost precedent level in the occupation of the accelerator, the first treatment room is required to at least wait until the treatment room that currently occupies the accelerator releases the occupation of the accelerator. Therefore, waiting time in the first treatment room 4A is made.

FIG. 2A shows a case where discontinuous multiportal irradiation control is applied to a patient A in the first treatment room 4A, the precedence of the first treatment room 4A and the precedence of the other second treatment 4B to the fourth treatment room 4D are the same and the assignment of the occupation of the accelerator is on the basis of the order of first arrival. In the case shown in FIG. 2A, when a remedial field in the first treatment room 4A is finished and the occupation of the accelerator is once released, it is required to wait to finish the occupation of the accelerator and the release of the occupation of the accelerator in the three treatment rooms from the second treatment room 4B to the fourth treatment room 4D until the accelerator is next occupied in the first treatment room 4A, and long waiting time is made.

FIG. 2B shows a case where discontinuous multiportal irradiation control is applied to the patient A in the first treatment room 4A and the precedence of the first treatment room 4A is set to "precedence: high (top priority)" that precedes the precedence of the other treatment rooms. In the case shown in FIG. 2B, a case where the remedial field is finished in the first treatment room 4A and the occupation of the accelerator is released will be considered. In this case, since the second treatment room 4B waits for the occupation of the accelerator and at that moment, the next remedial field is being prepared in the first treatment room 4A, no request for occupying the accelerator is output to the control system 3 and the first treatment room is not in a state waiting for the occupation of the accelerator. Therefore, the accelerator 1 is occupied by the second treatment room 4B. Then, when a request for occupying the accelerator in the first treatment room 4A is made again, the release of the occupation of the accelerator in the second treatment room 4B is required to be awaited to occupy the accelerator though the abovementioned request precedes a request for occupying the accelerator in the third treatment room 4C and the fourth treatment room 4D. Therefore, though waiting time is further reduced, compared with that in the case shown in FIG. 2A, it is difficult to reduce more of waiting time of the patient in the first treatment room 4A.

As described above, in the general discontinuous multiportal irradiation control, plural remedial fields are scheduled for the patient during treatment in the first treatment room 4A and there exists a case where time waiting for the occupation of the accelerator is made until preparation before remedial irradiation for executing irradiation in unexecuted remedial fields is finished and the accelerator is occupied since a request for occupying the accelerator in the first treatment room 4A is made again when the unexecuted remedial fields exist.

In the meantime, in the case of continuous multiportal irradiation control in this embodiment, when the control system recognizes the first treatment room 4A as a treatment room during continuous multiportal irradiation beforehand, the occupation of the accelerator in the first treatment room 4A is not released in a case where an unexecuted remedial field is left as shown in FIG. 3 even if a certain remedial field is finished in the first treatment room 4A, the next remedial field is advanced in the first treatment room 4A without being influenced by the other treatment room, and the accelerator is not occupied in the other treatment room until irradiation in all remedial fields is executed. Therefore, no waiting time for the occupation of the accelerator of the patient in the first treatment room 4A is made and treatment time is greatly reduced.

Next, a flow of irradiation in the particle beam treatment system in this embodiment will be described.

First, an ion (for example, a heavy particle ion such as a proton ion and a carbon ion) generated in the ion source is accelerated by the preceding-stage accelerator 1A. An ion beam radiated from the preceding-stage accelerator 1A is incident on the synchrotron 1B.

Energy is applied to the ion beam which is a charged particle beam by high-frequency power applied from a high frequency acceleration cavity 1B1 in the synchrotron 1B and the ion beam is accelerated. After the energy of the ion beam that orbits in the synchrotron 1B is amplified to set energy (for example, 100 to 200 MeV), a high frequency is applied to the ion beam from the high frequency applying device 1B2 for radiation. The ion beam that orbits within a stable limit transfers outside the stable limit by the application of the high frequency and is radiated from the synchrotron 1B through the deflector for radiation 1B3. In the radiation of the ion beam, current conducted to an electromagnet such as a four-pole electromagnet 1B5 and a deflecting electromagnet 1B4 provided to the synchrotron 1B is held at a current set value, and the stable limit is also held at an approximately fixed value. The radiation of the ion beam from the synchrotron 1B is stopped by stopping the application of the high-frequency power to the high frequency applying device 1B2.

The ion beam radiated from the synchrotron 1B is routed on the downstream side of the first beam routing subsystem 2E. The ion beam incident on the first beam routing subsystem 2E is selectively conducted to any of the irradiation devices 40A, 40B, 40C, 40D in the second beam routing subsystems 2A, 2B, 2C, 2D depending upon whether deflection operation is made by switching the excitation or the non-excitation of various electromagnets in the first beam routing subsystem 2E and the switching electromagnets 20A, 20B, 20C, 20D.

The ion beam incident on the treatment room 4A, 4B, 4C, 4D from the second beam routing subsystem 2A, 2B, 2C, 2D is radiated toward a target in a patient from the irradiation device 40A, 40B, 40C, 40D.

Next, a flow in remedial irradiation under the continuous multiportal irradiation control in this embodiment will be described, compared with a flow in remedial irradiation under the general discontinuous multiportal irradiation control, referring to FIGS. 4 and 5.

First, the flow in remedial irradiation under the general discontinuous multiportal irradiation control will be described, referring to FIG. 4.

First, the initiation of treatment is indicated by an operator (a step S40). Next, a request for occupying the accelerator is output to the control system 3 and the treatment room is turned a waiting state for the occupation of the accelerator (a step S41). Next, the occupation of the accelerator in another treatment room is finished and the treatment room is turned a state in which the accelerator is occupied (a step S42). Next, remedial irradiation is executed (a step S43). Then, the occupation of the accelerator is released on the basis of the termination of a remedial field (a step S44). Next, it is determined whether the next irradiation is scheduled or not (a step S45). When it is determined that the next irradiation is scheduled, processing is returned to the step S41 and the occupation of the accelerator is awaited again. In the meantime, when the schedule of irradiation is completely finished and it is determined that the next irradiation is not scheduled, the processing proceeds to a step S46 and the treatment is finished (the step S46).

Next, a flow in remedial irradiation under the continuous multiportal irradiation control in this embodiment will be described, referring to FIG. 5.

First, the initiation of treatment is indicated by an operator (a step S10).

Next, it is determined whether continuous multiportal irradiation control is executed or not (a step S11). When it is determined that the continuous multiportal irradiation control is executed, processing proceeds to a step S21, and when it is determined that discontinuous multiportal irradiation control is executed, the processing proceeds to a step S12.

For example, when treatment is applied to a certain specific patient in the certain treatment room 4A, 4B, 4C, 4D, setting in a prescription and setting of executing continuous multiportal irradiation control based upon selection by a therapist and specifications of the treatment room are input in this step S11. Further, when the accelerator is once occupied for remedial irradiation in the certain specific treatment room 4A, 4B, 4C, 4D on the basis of the selection of the therapist who applies particle beam therapy to a patient, a result of the selection that the continuous multiportal irradiation control is executed by the therapist is input in this step S11. Moreover, when the certain specific treatment room 4A, 4B, 4C, 4D occupies the accelerator 1, setting of executing continuous multiportal irradiation control in the treatment room 4A, 4B, 4C, 4D having a specific specification is input. In addition, when a certain specific prescription is applied to a patient in the unspecified treatment room 4A, 4B, 4C, 4D, setting of executing continuous multiportal irradiation control according to the specific prescription independent of the specifications of the treatment rooms 4A to 4D is input. Like these examples, flexible switching is enabled by outputting an instruction to the control system 3 via a terminal for operating the discontinuous multiportal irradiation control and the continuous multiportal irradiation control.

When it is determined that the continuous multiportal irradiation control is executed in the step S11, a request for occupying the accelerator is next output to the control system 3 (a step S21). Next, the occupation of the accelerator in another treatment room is finished and the certain treatment room is turned a state in which the accelerator is occupied (a step S22). Next, remedial irradiation is executed (a step S23). In this embodiment, a state in which the occupation of the accelerator is held is also kept after the remedial irradiation is finished in the step S23. Next, it is determined whether the next irradiation is scheduled or not (a step S24). When it is determined that the next irradiation is scheduled, the processing is returned to the step S23, the schedule of the next irradiation is prepared, and irradiation is executed. In the meantime, when the schedule of irradiation is completely finished and it is determined that the next irradiation is not scheduled, the processing proceeds to a step S25. Next, the occupation of the accelerator is released on the basis of the termination of all remedial fields (the step S25). Then, the treatment in the corresponding treatment room is finished (a step S30).

In the meantime, when it is determined in the step S11 that discontinuous multiportal irradiation control is executed, a request for occupying the accelerator is output to the control system 3 and the treatment room is turned a waiting state for the occupation of the accelerator (a step S12). Next, the occupation of the accelerator is finished in another treatment room and the treatment room is turned a state in which the accelerator is occupied (a step S13). Next, remedial irradiation is executed (a step S14). Then, the occupation of the accelerator is released on the basis of the termination of a remedial field (a step S15). Next, it is determined whether the next irradiation is scheduled or not (a step S16). When it is determined that the next irradiation is scheduled, the processing is returned to the step S11, and when it is determined that all the schedules of irradiation are finished and the next irradiation is not scheduled, the processing proceeds to the step S30.

Next, effects of this embodiment will be described.

As described above, in this embodiment, when plural remedial irradiation fields are required in a certain prescription and when an unexecuted remedial irradiation field is left in the same prescription even if a remedial irradiation field is finished, irradiation control (the continuous multiportal irradiation control) in which the occupation of the accelerator is not released is executed so as to settle the problem that treatment is not continuously made with the accelerator occupied for specific treatment under general irradiation control (the discontinuous multiportal irradiation control) in which the occupation of the accelerator is released every time a remedial irradiation field is finished.

All remedial irradiation fields included in a prescription can be accomplished without waiting for the elapse of time in which the accelerator is occupied by treatment in another treatment room by the release of the occupation of the accelerator by executing such continuous multiportal irradiation control except when a final remedial irradiation field that means the end of the prescription is finished, intentional operation to release the occupation of the accelerator or in the occurrence of system failure. That is, in treatment in which the continuous multiportal irradiation control is applied, once the accelerator is occupied, all remedial irradiation fields scheduled in the treatment can be ordinarily finished with the occupation of the accelerator maintained afterward and the reduction in treatment time of a specific patient can be realized.

For example, when treatment is applied to a specific patient, using an anesthetic together, a load onto the patient is reduced because an amount of the anesthetic applied to the specific patient is reduced by applying the continuous multiportal irradiation control and reducing treatment time. Further, the reduction in treatment time of an infant difficult to apply treatment in a patient treatment position in the treatment room in a state in which the infant is fixed for a longtime is another example of an effective utilization method.

For the currently executed irradiation method or the irradiation method executed in the past, a passive irradiation method in which an ion beam is scattered by a scatterer and the scattered beam irradiates an affected part by cancer in accordance with a shape of the affected part by cancer by the collimator is mainly adopted. In this passive irradiation, while a certain remedial irradiation field is finished and the next unexecuted remedial irradiation field is executed, an operator is required to perform work for accessing to the irradiation device and replacing collimators. Since time for the replacing work is required, it greatly contributes to the reduction of the whole treatment time that the occupation of the accelerator is released after a remedial irradiation field is finished and another treatment room occupies the accelerator. There are very few merits of occupying the accelerator.

However, in the scanning irradiation method in which a minute ion beam is scanned when a charged particle beam generated by the accelerator, and the like irradiates an affected part by cancer and irradiates the affected part by cancer, the ion beam is scanned by the scanning electromagnet. Therefore, while a certain remedial irradiation field is finished and the next unexecuted remedial irradiation field is executed, the operator is not required to access the irradiation device. Therefore, the scanning method can greatly contributes to the reduction in treatment time of a certain specific patient by executing the continuous multiportal irradiation control that all remedial irradiation fields scheduled in treatment are finished in a state in which the occupation of the accelerator is maintained as described above. Naturally, the passive irradiation method can also contribute to the reduction in treatment time of a certain specific patient by executing the continuous multiportal irradiation control.

Further, the control unit 3B of the control system 3 controls to keep a state in which the operation of the switching electromagnets 20A, 20B, 20C, 20D and the shutters 24A, 24B, 24C, 24D is maintained without changing the operation so that remedial irradiation in the treatment room that occupies the accelerator is more stably and securely executed while the occupation of the accelerator 1 is maintained, and can contribute to the reduction in treatment time of a specific patient.

The present invention is not limited to the abovementioned embodiment, and various variations and application are possible. The abovementioned embodiment has been described in detail to clarify the present invention and the present invention is not necessarily limited to an embodiment provided with the described all configurations.

For example, when the certain treatment room 4A, 4B, 4C, 4D once occupies the accelerator 1, the case where the continuous multiportal irradiation control is executed has been described except intentional operation to release the occupation of the accelerator or the occurrence of system failure. The control unit 3B of the control system 3 can control the beam routing system and the irradiation devices 40A, 40B, 40C, 40D to maintain the occupation of the accelerator 1 in any case until treatment prescribed for a specific patient is completely finished when the certain treatment room 4A, 4B, 4C, 4D of the plural treatment rooms 4A, 4B, 4C, 4D once occupies the accelerator 1 to treat the certain specific patient.

Effect that such the reduction in treatment time of a specific patient that is acquired in the abovementioned embodiment can be realized is also acquired by such control.

What is claimed is:

1. A particle beam treatment system, comprising:
   an accelerator that radiates a charged particle beam;
   a plurality of treatment rooms in each of which an irradiation device that irradiates with the charged particle beam is arranged, wherein the irradiating device is provided with scanning electromagnets to scan the charged particle beam to a patient;
   a beam routing system which is connected to the accelerator and which separately routes the charged particle beam radiated from the accelerator to each irradiation device in the plurality of treatment rooms; and
   a control system that controls the accelerator, the beam routing system and the irradiation devices,
   wherein the control system controls the beam routing system and the irradiation device so as to occupy the accelerator for the plurality of treatment rooms according to one of discontinuous multiportal irradiation control and continuous multiportal irradiation control except for an intentional operation to release the occupation of the accelerator or the occurrence of system failure;
   wherein treatment prescribed for a patient includes a plurality of irradiations which require occupation of the accelerator, and the plurality of irradiations are separated by preparations which do not require occupation of the accelerator;
   wherein the control system maintains occupation of the accelerator for a certain treatment room when the continuous multiportal irradiation control is requested, so that the accelerator is occupied for the certain treatment room after completion of one irradiation of the plurality of irradiations for the patient according to the prescribed treatment at the certain treatment room, and the control system determines whether a next irradiation of the plurality of the irradiations for the patient according to the prescribed treatment is scheduled for the certain treatment room and, if yes, executes the next irradiation for the certain treatment room without releasing the occupation of the accelerator for the certain treatment room during one of the preparations between the one irradiation that is completed and the next irradiation that has been determined to be scheduled to begin after the one of the preparations thereby maintaining occupation of the accelerator for the certain treatment room from the one irradiation to the next irradiation in the certain treatment room, and, if no, the control system releases the occupation of the accelerator for the certain treatment room.

2. The particle beam treatment system according to claim 1,
   wherein the control system controls the beam routing system and the irradiation device so as to maintain the occupation of the accelerator until treatment prescribed for a certain specific patient is completely finished when treatment is carried out for the certain specific patient in the certain treatment room.

3. The particle beam treatment system according to claim 1,
wherein the control system controls the beam routing system and the irradiation device so as to maintain the occupation of the accelerator on the basis of the selection of a therapist until predetermined irradiation is completely finished.

4. The particle beam treatment system according to claim 1,
wherein the control system controls the beam routing system and the irradiation device so as to maintain the occupation of the accelerator in a specific treatment room when the specific treatment room of the plurality of treatment rooms occupies the accelerator.

5. The particle beam treatment system according to claim 1,
wherein the control system controls the beam routing system and the irradiation device so as to maintain the occupation of the accelerator until treatment in a certain specific prescription is completely finished when the certain specific prescription is applied to a patient in an unspecified treatment room.

6. The particle beam treatment system according to claim 1,
wherein the beam routing system is provided with:
a first beam routing subsystem which is connected to the accelerator and which routes the charged particle beam radiated from the accelerator;
a plurality of second beam routing subsystems which are connected to the first beam routing subsystem and which route the charged particle beam routed by the first beam routing subsystem to the irradiation device arranged in the treatment room; and
path switching devices respectively arranged in each joint of a beam path of the first beam routing subsystem and beam paths of the plurality of second beam routing subsystems for switching the beam paths for conducting the charged particle beam,
wherein the control system controls the operation of the path switching device to keep a state in which the operation is maintained without being changed while the occupation of the accelerator is maintained.

7. The particle beam treatment system according to claim 6,
wherein the beam routing system is further provided with shutters provided to the plurality of respective second beam routing subsystems for shutting off the beam paths of the second beam routing subsystem; and
the control system controls the operation of the shutter to keep a state in which the operation is maintained while the occupation of the accelerator is maintained.

8. The particle beam treatment system according to claim 1,
wherein, under discontinuous multiportal irradiation control, the control system controls the beam routing system and the irradiation device so as to release the occupation of the accelerator for the certain treatment room after completion of one irradiation at the certain treatment room, and if a next irradiation is scheduled for the certain treatment room, then wait for the accelerator to become available before the certain treatment room occupies the accelerator again to execute the next irradiation.

9. The particle beam treatment system according to claim 1,
wherein the preparations include at least one of positioning or imaging.

10. A particle beam treatment system, comprising:
an accelerator that radiates a charged particle beam;
a plurality of treatment rooms in each of which an irradiation device that irradiates with the charged particle beam is arranged, wherein the irradiating device is provided with scanning electromagnets to scan the charged particle beam to a patient;
a beam routing system which is connected to the accelerator and which separately routes the charged particle beam radiated from the accelerator to each irradiation device in the plurality of treatment rooms; and
a control system that controls the accelerator, the beam routing system and the irradiation devices,
wherein the control system controls the beam routing system and the irradiation device so as to occupy the accelerator for the plurality of treatment rooms according to one of discontinuous multiportal irradiation control and continuous multiportal irradiation control except for an intentional operation to release the occupation of the accelerator or the occurrence of system failure;
wherein treatment prescribed for the specific patient includes a plurality of irradiations which require occupation of the accelerator, and the plurality of irradiations are separated by preparations which do not require occupation of the accelerator; and
wherein the control system maintains the occupation of the accelerator for a certain treatment room when the continuous multiportal irradiation control is requested, so that the accelerator is occupied for the certain treatment room after completion of one irradiation of the plurality of irradiations according to the prescribed treatment for the specific patient at the certain treatment room, and if the treatment prescribed for the specific patient is not completely finished, the control system executes the next irradiation of the plurality of irradiations according to the prescribed treatment for the specific patient in the certain treatment room without releasing the occupation of the accelerator for the certain treatment room during one of the preparations between the one irradiation that is completed and the next irradiation that has been determined to be scheduled to begin after the one of the preparations thereby maintaining occupation of the accelerator for the certain treatment room from the one irradiation to the next irradiation in the certain treatment room, until all irradiations of the treatment prescribed for the specific patient are executed, and, if the treatment prescribed for the specific patient is completely finished, the control system releases the occupation of the accelerator for the certain treatment room.

11. The particle beam treatment system according to claim 10,
wherein the beam routing system is provided with:
a first beam routing subsystem which is connected to the accelerator and which routes the charged particle beam radiated from the accelerator;
a plurality of second beam routing subsystems which are connected to the first beam routing subsystem and which route the charged particle beam routed by the first beam routing subsystem to the irradiation device arranged in the treatment room; and
path switching devices respectively arranged in each joint of a beam path of the first beam routing subsystem and beam paths of the plurality of second beam routing subsystems for switching the beam paths for conducting the charged particle beam, wherein the control system controls the operation of the path switching device to keep a state in which the operation is maintained without being changed while the occupation of the accelerator is maintained.

12. The particle beam treatment system according to claim 11, wherein the beam routing system is further provided with shutters provided to the plurality of respective second beam routing subsystems for shutting off the beam paths of the second beam routing subsystem; and the control system controls the operation of the shutter to keep a state in which the operation is maintained while the occupation of the accelerator is maintained.

13. The particle beam treatment system according to claim 10, wherein, under discontinuous multiportal irradiation control, the control system controls the beam routing system and the irradiation device so as to release the occupation of the accelerator for the certain treatment room after completion of one irradiation to treat the specific patient at the certain treatment room, and if the treatment prescribed for the specific patient is not completely finished, then wait for the accelerator to become available before the certain treatment room occupies the accelerator again to execute a next irradiation.

14. The particle beam treatment system according to claim 10, wherein the preparations include at least one of positioning or imaging.

15. A particle beam treatment system, comprising:

an accelerator that radiates a charged particle beam;

a plurality of treatment rooms in each of which an irradiation device that irradiates with the charged particle beam is arranged, wherein the irradiating device is provided with scanning electromagnets to scan the charged particle beam to a patient;

a beam routing system which is connected to the accelerator and which separately routes the charged particle beam radiated from the accelerator to each irradiation device in the plurality of treatment rooms; and a control system that controls the accelerator, the beam routing system and the irradiation devices, wherein the control system controls the beam routing system and the irradiation device so as to occupy the accelerator for the plurality of treatment rooms according to one of discontinuous multiportal irradiation control and continuous multiportal irradiation control except for an intentional operation of a therapist to release the occupation of the accelerator or the occurrence of system failure;

wherein the predetermined irradiation treatment for the patient includes a plurality of irradiations which require occupation of the accelerator, and the plurality of irradiations are separated by preparations which do not require occupation of the accelerator; and wherein the control system maintains occupation of the accelerator for a certain treatment room on the basis of the selection of a therapist selecting the continuous multiportal irradiation control, so that the accelerator keeps the accelerator occupied for the certain treatment room after completion of one irradiation of the plurality of irradiations according to the predetermined irradiation treatment for the patient at the certain treatment room, and if the predetermined irradiation treatment for the patient is not completely finished, the control system executes a next irradiation of the plurality of irradiations according to the predetermined irradiation treatment for the certain treatment room without releasing the occupation of the accelerator for the certain treatment room during one of the preparations between the one irradiation that is completed and the next irradiation that has been determined to be scheduled to begin after the one of the preparations thereby maintaining occupation of the accelerator for the certain treatment room from the one irradiation to the next irradiation in the certain treatment room, and, if the predetermined irradiation treatment for the patient is completely finished, the control system releases the occupation of the accelerator for the certain treatment room.

16. The particle beam treatment system according to claim 15, wherein the beam routing system is provided with:

a first beam routing subsystem which is connected to the accelerator and which routes the charged particle beam radiated from the accelerator;

a plurality of second beam routing subsystems which are connected to the first beam routing subsystem and which route the charged particle beam routed by the first beam routing subsystem to the irradiation device arranged in the treatment room; and path switching devices respectively arranged in each joint of a beam path of the first beam routing subsystem and beam paths of the plurality of second beam routing subsystems for switching the beam paths for conducting the charged particle beam, wherein the control system controls the operation of the path switching device to keep a state in which the operation is maintained without being changed while the occupation of the accelerator is maintained.

17. The particle beam treatment system according to claim 16, wherein the beam routing system is further provided with shutters provided to the plurality of respective second beam routing subsystems for shutting off the beam paths of the second beam routing subsystem; and the control system controls the operation of the shutter to keep a state in which the operation is maintained while the occupation of the accelerator is maintained.

18. The particle beam treatment system according to claim 15, wherein, under discontinuous multiportal irradiation control, the control system controls the beam routing system and the irradiation device so as to release the occupation of the accelerator for the certain treatment room after completion of one irradiation to treat the patient at the certain treatment room, and if the predetermined irradiation treatment is not completely finished, then wait for the accelerator to become available before the certain treatment room occupies the accelerator again to execute a next irradiation.

19. The particle beam treatment system according to claim 15, wherein the preparations include at least one of positioning or imaging.

* * * * *